United States Patent [19]  
Thrun

[11] 4,058,425  
[45] Nov. 15, 1977

[54] INHALANT DISPERSER
[75] Inventor: James L. Thrun, Orchard Park, N.Y.
[73] Assignee: A-T-O Inc., Willoughby, Ohio
[21] Appl. No.: 452,079
[22] Filed: Mar. 18, 1974

Related U.S. Application Data
[62] Division of Ser. No. 379,362, July 16, 1973, Pat. No. 3,881,634.

[51] Int. Cl.² .................... B29D 23/00; B31F 1/00
[52] U.S. Cl. .................... 156/200; 156/203; 156/204; 156/291
[58] Field of Search ............ 156/290, 291, 226, 227, 156/204, 200–201, 203; 222/107, 5; 53/28, 21 FC; 128/260, 270, 272, 200, 198, 206; 206/484

[56] References Cited
U.S. PATENT DOCUMENTS

| | | | |
|---|---|---|---|
| 2,173,528 | 9/1939 | Beale | 53/21 FC X |
| 2,209,914 | 7/1940 | Gerber et al. | 128/272 |
| 2,395,109 | 2/1946 | Fonda | 128/200 |
| 2,546,848 | 3/1951 | Bishop | 206/530 X |
| 2,579,403 | 12/1951 | Slomowitz et al. | 128/260 X |
| 2,627,341 | 2/1953 | Morgan | 206/439 |
| 2,681,168 | 6/1954 | McMillion | 222/107 X |
| 3,082,585 | 3/1963 | Waters | 53/28 X |
| 3,121,249 | 2/1964 | Affleck et al. | 156/291 X |
| 3,123,210 | 3/1964 | Hermanson et al. | 206/439 X |
| 3,476,506 | 11/1969 | Andersen et al. | 53/21 FC X |
| 3,595,468 | 7/1971 | Repko | 229/55 X |
| 3,702,677 | 11/1972 | Heffington | 239/55 |
| 3,856,142 | 12/1974 | Vessalo | 206/484 X |

FOREIGN PATENT DOCUMENTS

| 1,320,316 | 1/1963 | France | 206/438 X |
|---|---|---|---|

Primary Examiner—David A. Simmons  
Attorney, Agent, or Firm—Christel & Bean

[57] ABSTRACT

An inhalant disperser comprising an ampoule contained within an enclosure formed of an outer layer of liquid absorbent paper and an inner layer of material having an impermeable portion confining the fragments of a broken ampoule within the enclosure and a perforated portion permitting the passage of the ampoule contents therethrough for permeating the outer layer.

3 Claims, 7 Drawing Figures

INHALANT DISPERSER

CROSS REFERENCE TO A RELATED APPLICATION

This application is a dvision of application Ser. No. 379,362 filed July 16, 1973, now U.S. Pat. No. 3,881,634.

BACKGROUND OF THE INVENTION

This invention relates generally to a disperser and, more particularly, to an inhalant disperser for dispelling vaporizable liquids.

Inhalant dispersers or inhalators for releasing ammonia or medicated vapors for treating persons suffering from fainting spells and the like are well known. Such devices generally comprise an inner container or ampoule of a frangible material containing a vaporizable liquid and encapsulated within a liquid absorbent material, such as cotton for example. In use, the container is broken to release the liquid, which is absorbed by the cotton and dispelled as a vapor through the porous cotton material. While many such inhalators are admirably suited for their intended purposes, they possess certain disadvantages. For example, the cotton fabric often is saturated with a starch solution prior to tightly wrapping the same about the container. After wrapping, the package is dried under controlled temperatures to substantially rigidify and strengthen the finished product. The starch tends to close the pores of the cotton material and retards, to some degree, subsequent impregnation thereof by the liquid solution released from the container. This, in turn, retards the escape of vapors for inhalation by the user.

In another approach, the step of wetting the cotton material with a starch solution is eliminated. Instead, the strip of cotton is wrapped loosely about the frangible container and then bound by a fabric netting, which confines the cotton material and serves as a container for the finished product. While such packaged inhalators do speed up liquid impregnation of the cotton material and consequent vaporization, they do not effectively confine the fragments of the broken container thereby subjecting the user to possible injury.

SUMMARY OF THE INVENTION

A primary object of the present invention is to provide a simple and improved inhalant disperser which obviates the above disadvantages and provides virtually instant vaporization upon release of the ampoule contents.

Another object of this invention is to provide the foregoing disperser with a protective enclosure for effectively confining the fragments of a broken ampoule within the disperser package while readily permitting the escape of vapors therefrom.

A further object of the present invention is to provide an inhalant disperser which is simple and strong in construction, sufficiently durable and rugged to withstand abuse during handling without damaging the inner frangible ampoule, relatively low in costs, and which is well adapted to commercial mass production by known manufacturing techniques.

In one aspect thereof, the inhalant disperser of this invention is characterized by an enclosure formed of filter paper and provided with an inner protective layer of material confining the ampoule fragments within the enclosure while permitting the dispersion of vapors outwardly therethrough.

The foregoing and other objects, advantages, and characterizing features of the present invention will become clearly apparent from the ensuing detailed description of illustrative embodiments thereof, taken together with the accompanying drawing wherein like reference characters denote like parts throughout the various views.

BRIEF DESCRIPTION OF THE DRAWING FIGURES

DETAILED DESCRIPTION OF AN ILLUSTRATIVE EMBODIMENT

Figure 1:
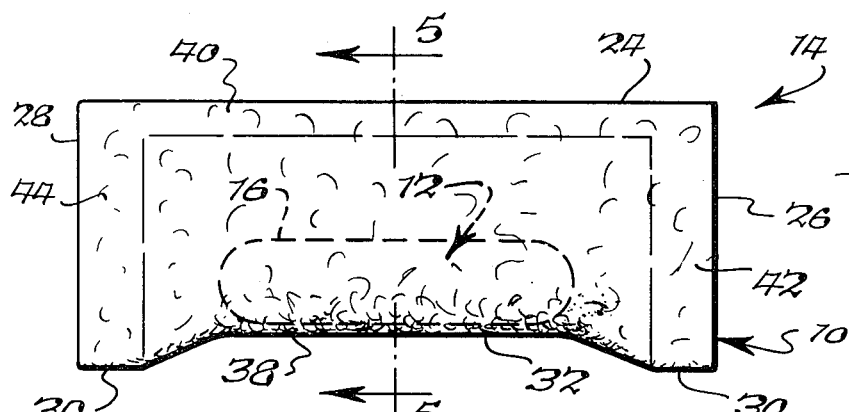
FIG. 1 is a front elevational view of an inhalant disperser constructed in accordance with this invention.
Figure 2:
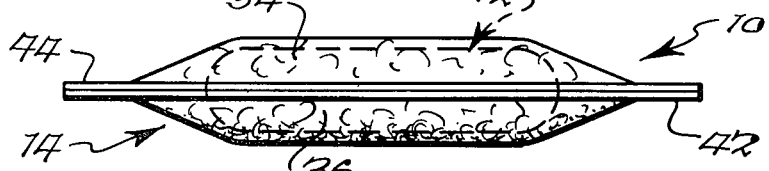
FIG. 2 is a top plan view thereof.
Figure 3:
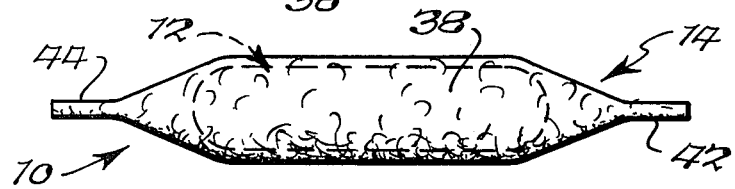
FIG. 3 is a bottom plan view thereof.

Referring now in detail to the illustrative embodiment depicted in the accompanying drawing, there is shown in FIG. 1 an inhalant disperser, generally designated 10, constructed in accordance with this invention, comprising a frangible or breakable ampoule 12 completely enclosed within a protective covering or enclosure 14 in the form of an envelope package.

Ampoule 12 comprises an hermetically sealed tubular casing 16 preferably formed of onion skin glass and having a relatively thin wall 18 (FIG. 5) so as to be easily breakable upon the application of pressure by the user's fingers. However, the ampoule wall is sufficiently strong to withstand, in a vacuum chamber, a pressure of 1.68 psia, which is the equivalent of subjecting the ampoule to an altitude of 50,000 feet.

Ampoule 12 contains an ammonia solution which, when released, readily evaporates for emergency inhalation by persons subjected to fainting spells and the like. However, it should be understood that the ampoule incorporated in the disperser of this invention can be filled with various vaporizable liquids or medicaments, as desired, such as stimulants for patients having a heart condition or for treating nasal and pulmonary afflictions, for example.

The protective enclosure 14 is formed of a strip of a suitable liquid absorbent filter paper 20 constituting the outer layer of enclosure 14 and having an inner layer or film 22 (FIG. 6) of an impermeable material adhered thereto as will hereinafter be more fully described. As shown in FIG. 1, enclosure 14 comprises a body having a generally rectangular outline in elevation and provided with an upper longitudinal edge 24, a pair of opposite ends 26 and 28, and a lower longitudinal edge 30 formed with a central, recessed rounded edge 32 therein. The terms upper, lower, top, bottom and the like, as used herein, are applied only for convenience of description with reference to FIG. 1 of the drawing and are not used in a limiting sense.

Figure 4:
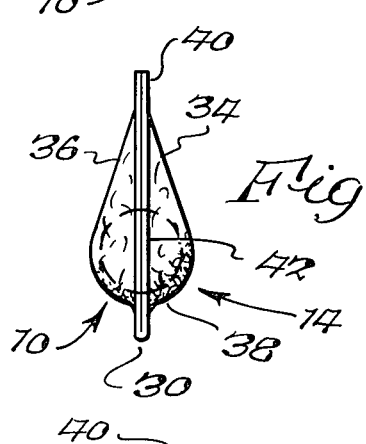
FIG. 4 is an end elevational view thereof.

Enclosure 14 is provided with opposed walls 34 and 36 (FIG. 4 and 5) extending from the rounded, common, lower edge 32 upwardly and around the sides of ampoule 12, and then upwardly at an angle in a converging relation to a common upper juncture formed by the overlapping ends of walls 34 and 36, which are sealed together along strip portion 40 extending lengthwise of enclosure 14 adjacent the upper edge 24 thereof. The opposite ends of enclosure walls 34 and 36 also are sealed together along strip portions 42 and 44 extending transversely of enclosure 14 adjacent the opposite ends thereof to complete the enclosure. The lower rounded edge 32 of enclosure 14 forms a bulbous portion 38 fitting snugly about the major portion of ampoule 12 to maintain the latter substantially fixed in position within enclosure 14.

Figure 6:
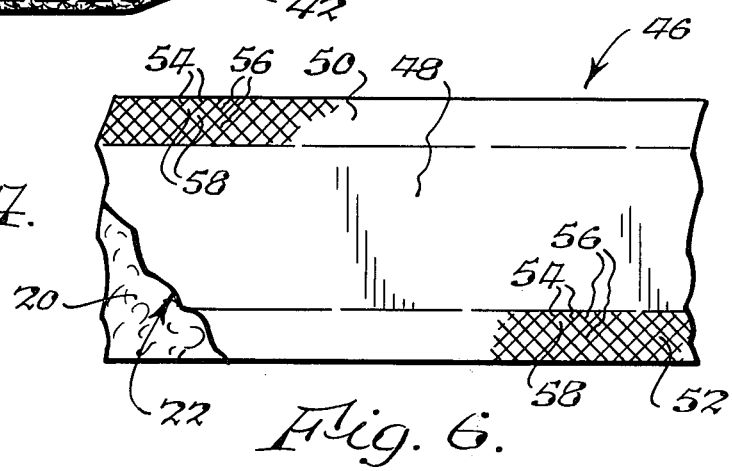
FIG. 6 is a fragmentary view of a strip of material forming the disperser package, showing a major portion of the inner layer and a small portion of the outer layer.

In forming the disperser package, an elongated strip 46 of a suitable liquid absorbent filter paper 20 is coated with a suitable "hot melt" adhesive to form inner layer 22. As used herein, a "hot melt" adhesive is one that liquifies at certain elevated temperatures and becomes readily fusible. As shown in FIG. 6, the elongated central area of strip 46 is completely covered with the desired adhesive to eliminate any voids and form an impermeable central barrier or liner 48 preventing the passage of any glass particulates therethrough. This coating of adhesive on the inner surface of the filter paper strip 46 strengthens the same and inhibits the tearing or destruction thereof. The remaining area of strip 46 is only partially covered with adhesive to form apertured bands 50 and 52 extending lengthwise of strip 46 along the opposite longitudinal edges thereof. As shown diagrammatically in FIG. 6, the adhesive deposited on bands 50 and 52 preferably is in the form of a pattern comprising diagonally extending, intersecting lines 54 and 56 defining a multiplicity of diamond shaped openings or apertures 58 therebetween for the passage of the ampoule liquid contents therethrough. Preferably, approximately 50 percent of the area of bands 50 and 52 is covered with adhesive, the remainder being left open to provide the desired passages. This partial covering of paper 20 along bands 50 and 52 also serves to strengthen the same and maintain the integrity thereof.

Figure 5:
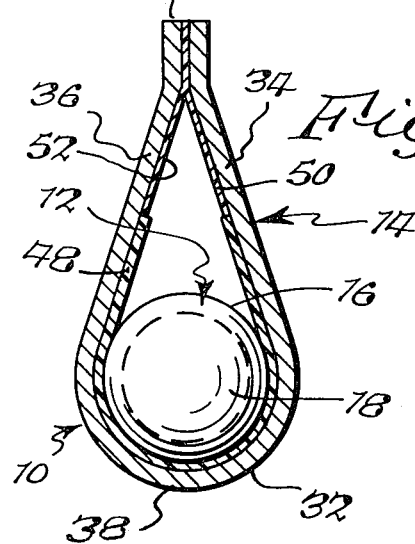
FIG. 5 is a transverse cross sectional view, on an enlarged scale, taken about on line 5—5 of FIG. 1.

After the adhesive coating operation, strip 46 can be severed at equally spaced longitudinal intervals to form discrete lengths thereof. Each such length is then folded lengthwise or along its longitudinal axis to form an elongated trough formation for receiving an ampoule 12 therein. After ampoule 12 is placed in the trough formation, the opposite longitudinal edges of the strip are brought together and heat sealed, as at 40, in a conventional manner, the adhesive along such edges fusing together upon the application of heat thereto. Simultaneously, the opposite ends of the folded strip are heat sealed along strips 42 and 44 in the same manner to complete enclosure 14. As shown in FIG. 5, the bulbous portion 38 of folded enclosure 14 snugly engages the periphery of ampoule 12 along a major portion thereof to substantially retain the latter in a fixed position therein.

In a commercial, mass production operation, strip 46 can be severed into discrete lengths after the heat sealing operation. In such an operation, an elongated, continuous flat strip of filter paper 20 of the desired width and gauge is continuously advanced longitudinally and coated with adhesive to form the central impermeable barrier portion 48 and the apertured bands 50 and 52 in the pattern illustrated in FIG. 6.

As the adhesively coated strip advances, it passes through a folding station wherein the opposite longitudinal edges of strip 46 are urged toward each other to form an elongated trough along the longitudinal axis of strip 46. Ampoules 12 are then deposited in the trough at selective, equally spaced distances during continued advancement of strip 46. At the next downstream station, the longitudinal edges of the strip 46 are brought together and heat sealed along such edges and along equally spaced, transverse strips extending crosswise of the folded strip and between each adjacent pair of longitudinally spaced ampoules 12. Subsequently, the folded and sealed strip is severed into discrete lengths along transverse lines centrally of the transversely extending sealed strips to form the finished, packaged dispersers 10.

In use, the frangible ampoule 12 is crushed or broken by the pressure of the user's fingers to release the liquid contents thereof. The liquid flows through openings 58 and is absorbed by filter paper 20 for release as vapor. The solid, central, impermeable barrier 48 located about bulbous portion 38 prevents the egress of the ampoule fragments outwardly through enclosure 14 to avoid injury to the user's fingers while the large open area defined by the multiplicity of openings 58 in apertured bands 50 and 52 permits rapid flow of the liquid therethrough for quickly permeating filter paper 20. The liquid immediately spreads and diffuses throughout filter paper 20 and is released therefrom as vapors for inhalation by the user. Disperser 10 provides virtually instant vaporization upon breakage of ampoule 12. While the diamond-shaped pattern on bands 50 and 52 illustrated in FIG. 6 is preferable for maximum protection against glass fragmentation and optimum flow of the ampoule contents in the finished product, it should be understood that various designs may be utilized so long as a sufficiently large total open area is provided for relatively unrestricted flow of the ampoule contents therethrough.

As shown in FIG. 5, the impermeable barrier 48 extends about pocket 38, around and well beyond the periphery of ampoule 12 to insure retention of the ampoule fragments within the confines of enclosure 14. Moreover, enclosure 14 tightly embraces ampoule 12 over a major portion of its circumferential periphery and overlies the upper side portions thereof, as viewed in FIG. 5, to retain ampoule 12 in a substantially fixed position within enclosure 14, thereby minimizing the possibility of accidentally bursting ampoule 12. Moreover, the relatively wide sealing strips or areas along the three edges of enclosure 14 render the latter sufficiently stiff and rigid to withstand normal handling without damage to ampoule 12.

The particular shape of enclosure 14, i.e. the generally rectangular configuration thereof providing a large width relative to the length enables disperser 10 to be conveniently handled by human fingers for effective use.

While ampoule 12 of disperser 10 preferably is filled with an ammonia solution or other suitable vaporizable medicament, it should be understood that other commercial vaporizable solutions, such as perfumes or deodorants for example, can be contained therein, as desired. Also, the relatively wide, flat sealed strip portions can be effectively used as applicators when saturated with the ampoule contents, for applying the latter to human or other surfaces.

Figure 7:
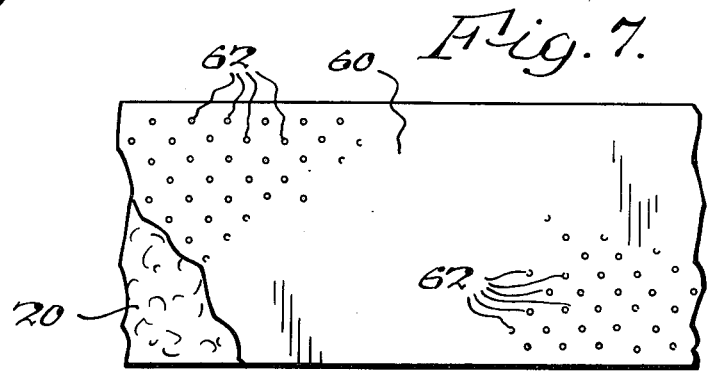
FIG. 7 is a view similar to FIG. 6, showing another form of inner layer for the strip of material forming the disperser package.

FIG. 7 illustrates another form of the invention in which the inner layer of material applied to filter paper 20 is a relatively thin film or liner 60 of thermoplastic material, such as polyethylene for example, in lieu of an adhesive. The thermoplastic film 60 in strip form is laminated or otherwise applied to filter paper 20 and is folded lengthwise therewith to provide a trough formation for the reception of ampoules 12. The longitudinal edges of the composite strip are then heat sealed together, the thermoplastic material along such edges fusing together upon the application of heat thereto. Also, the opposite ends of the folded strip are heat sealed in a similar manner to complete the enclosure.

A multiplicity of perforations in the form of closely spaced, minute apertures 62 are formed in liner 60 for the passage of the ampoule contents therethrough. These apertures 62 can be spaced over the entire liner area and made small enough to preclude the passage of ampoule fragments therethrough while permitting the flow of the ampoule contents therethrough. The total open area defined by apertures 62 is sufficiently large to facilitate rapid saturation of filter paper 20 by the ampoule contents. Alternately, apertures 62 can be made relatively large and located only in the areas along the opposite longitudinal edges of the strip in the same manner as apertured bands 50 and 52 are formed. In any event, the number and placement of apertures 62 in liner 60 is such as to effect immediate flow of the ampoule contents therethrough upon the release thereof from ampoule 12 to allow rapid impregnation of filter paper 20 and virtually instantaneous dispersement of the fumes or vapors therefrom.

Apertures 62 can be formed in liner 60 prior to or after the application thereof to filter paper 20, as desired. This form of the invention also lends itself to commercial mass production in the same manner described above in connection with the first form of the disperser described.

From the foregoing, it is apparent that the objects of the present invention have been fully accomplished. As a result of this invention, an improved inhalant disperser is provided for rapidly dispelling vapors upon release of the ampoule contents while confining the fragments of a broken ampoule safely within the protective enclosure of the disperser. The disperser package can be conveniently handled and is sufficiently stiff and rigid to withstand normal handling without damaging the ampoule contained therein.

Preferred embodiments of this invention having been disclosed in detail, it is to be understood that this has been done by way of illustration only.

I claim:

1. A method of forming an inhalant disperser comprising: applying a protective layer of impermeable material on a strip of liquid absorbent paper to form a composite multi-layered strip wherein said protective layer of material is an adhesive applied as a solid coating along the central portions of said strip of paper and as apertured bands on the remaining portions of said strip; folding said composite strip lengthwise to form a trough with said protective layer constituting the inner wall of said trough; placing an ampoule containing a vaporizable liquid in said trough; said trough being shaped to engage a major portion of said ampoule; and sealing said folded composite strip along the open edges thereof to form an enclosure for said ampoule, said adhesive on said strip being meltable under elevated temperatures to effect said sealing of said open edges upon the application of heat thereto in a manner wherein said vaporizable liquid may pass readily through at least portions of said apertured bands.

2. A method of forming an inhalant disperser comprising: applying a protective layer of impermeable material on a strip of liquid absorbent paper to form a composite multilayered strip wherein said protective layer of material is provided with a multiplicity of closely spaced apertures over the entire surface thereof; folding said composite strip lengthwise to form a trough with said protective layer constituting the inner wall of said trough; placing an ampoule containing a vaporizable liquid in said trough; said trough being shaped to engage a major portion of said ampoule; and sealing said folded composite strip along the open edges thereof to form an enclosure for said ampoule, said protective layer on said strip being meltable under elevated temperatures to effect said sealing of said open edges upon the application of heat thereto in a manner wherein said vaporizable liquid may pass readily through at least portions of said apertures.

3. A method according to claim 2 wherein said protective layer of material is a film of thermoplastic material laminated on said strip of paper; said thermoplastic material being fusible along said open edges upon the application of heat thereto.

* * * * *